(12) United States Patent
Leisner et al.

(10) Patent No.: US 6,626,878 B1
(45) Date of Patent: Sep. 30, 2003

(54) OSTOMY APPLIANCE WITH PERFORATED FLANGE

(75) Inventors: Henrik Leisner, Gentofte (DK); Michael Hansen, Gilleleje (DK)

(73) Assignee: Coloplast A/S, Humlebaek (DK)

(*) Notice: Subject to any disclaimer, the term of this patent is extended or adjusted under 35 U.S.C. 154(b) by 0 days.

(21) Appl. No.: 09/850,744

(22) PCT Filed: Nov. 16, 1999

(86) PCT No.: PCT/DK99/00630
§ 371 (c)(1),
(2), (4) Date: May 21, 2001

(87) PCT Pub. No.: WO00/30576
PCT Pub. Date: Jun. 2, 2000

(30) Foreign Application Priority Data

Nov. 19, 1998 (DK) .................................. 1998 01520

(51) Int. Cl.⁷ .................................................. A61F 5/44
(52) U.S. Cl. ...................... 604/339; 604/332; 604/342; 604/344
(58) Field of Search ................ 604/332–345, 604/322, 324, 326, 327

(56) References Cited

U.S. PATENT DOCUMENTS

| | | | | |
|---|---|---|---|---|
| 3,667,469 A | * | 6/1972 | Marsan | 604/336 |
| 4,723,952 A | * | 2/1988 | Esposito | 604/338 |
| 5,203,806 A | * | 4/1993 | Broida | 604/338 |
| 5,352,316 A | * | 10/1994 | Steer | 156/252 |
| 5,486,158 A | * | 1/1996 | Samuelsen | 602/46 |
| 5,545,154 A | * | 8/1996 | Oberholtzer | 604/336 |
| 5,714,225 A | | 2/1998 | Hansen et al. | 428/114 |
| 5,865,819 A | * | 2/1999 | Cisko et al. | 604/327 |
| 6,106,507 A | * | 8/2000 | Botten et al. | 604/338 |

FOREIGN PATENT DOCUMENTS

| | | | |
|---|---|---|---|
| EP | 0 276 043 | 7/1988 | |
| EP | 0276043 | * 7/1988 | ............ A61F/5/445 |
| EP | 0 793 951 | 9/1997 | |
| GB | 2 283 916 | 5/1995 | |
| WO | 94/15562 | 7/1994 | |
| WO | 96/38106 | 12/1996 | |
| WO | WO 96/38106 | * 12/1996 | ............ A61F/5/448 |
| WO | 9638106 | * 12/1996 | ............ A61F/5/448 |
| WO | 98/34573 | 8/1998 | |

* cited by examiner

*Primary Examiner*—Michael Mar
*Assistant Examiner*—Amanda Flynn
(74) *Attorney, Agent, or Firm*—Jacobson Holman PLLC

(57) ABSTRACT

An ostomy appliance having a body side member with an adhesive wafer or pad for securing the appliance to the user's skin, the wafer or pad having a hole for receiving a stoma, and a separately exchangeable collecting bag secured to the body side ostomy member for receiving secretions from the ostomy. The body side member includes a first flange connected thereto via a first connecting section and the collecting bag includes a second substantially annular flange which is connected to the collecting bag via a substantially annular second connecting section. The annular second flange is radially divided into an inner portion and an outer portion by at least one opening therethrough in an essentially circular zone corresponding to or larger than the outer radius of the first connecting section which reduces the risk of leakage and also reduces the necessary cleaning when substituting the collecting bag.

20 Claims, 4 Drawing Sheets

OSTOMY APPLIANCE WITH PERFORATED FLANGE

FIELD OF THE INVENTION

The present invention relates to an ostomy appliance comprising a body side member comprising an adhesive wafer or pad for securing the appliance to the user's skin, said wafer or pad having a hole for receiving a stoma, and a separately exchangeable receiving bag secured to the body side ostomy member for receiving secretions from the ostomy, wherein the body side member comprises a first substantially annular first flange which is fixedly connected to the base plate and the receiving bag comprises a substantially annular second flange adapted for removable and adhesive coupling and sealing to said fist flange.

DESCRIPTION OF THE RELATED ART

In connection with surgery for a number of diseases in the gastrointestinal tract a consequence is, in many cases, that the colon, the ileum or the urethra has been exposed surgically and the patient is left with an abdominal stoma and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma. Also in connection with a fistula, the patient will have to rely on an appliance to collect the bodily material emerging from such opening.

Ostomy appliances are well known. Such appliances may be two-piece or one-piece appliances. In both types of appliances, a body side member is attached to the wearer's abdomen, and optionally a receiving member or bag is attached to the body side ostomy member for receiving exudates from the ostomy in case of a two-piece appliance.

When using one-piece appliances, the whole appliance, including the adhesive wafer or pad securing the appliance to the skin is removed and replaced by a fresh appliance. When using two-piece appliances, a body side ostomy member or carrier device is left in place for several days, and only the receiving member or bag is replaced.

The service time of the body side ostomy member depends on the amount and aggressiveness of the exudates and of the tightness between the ostomy and the body side ostomy member.

In a collecting system of this type known from EP patent application No. 0 276 043, a flange for adhesive connection with the flange of the collecting bag or with the bag itself being fastened on a base plate in the form of an adhesive pad.

In such a collecting system, the base plate of the carrier device must be able to remain on the user over a long period of time, for example up to 8–10 days. During this whole period of time, the carrier device must be capable of undergoing deformation owing to the user's movements, washing, exposure to bag replacements, etc. Conventionally, the base plate of such a carrier device is designed as a thin adhesive foil, optionally with some sort of stiffening reinforcement disc for maintaining a plane adhesive surface for the bag. However, such a reinforcement disc prevents the base plate from following the contours of the body when the user moves, and it does not provide the desired shock absorbing effect between the collecting bag and the user, which, of course, reduces comfort. A less rigid disc would be able to follow the base plate during such movements, to be sure, but would thus exert a pull in it, which, in addition to transmitting an unpleasant pulling effect to the user's skin, also weakens the adhesive effect between base plate and skin. Furthermore, the adhesive surface facing the bag will not in that case remain plane owing to the inevitable deformations, which results in problems of rearranging the bag on the user.

In the above EP patent application, an attempt has been made to eliminate these problems by connecting a rigid flange with the base plate via a flexible sheet, which, however, provides an unstable and insecure connection. Furthermore, the adhesive connection taught between bag and carrier device is provided either by a number of layers of adhesive applied to the flange of the base plate and activated one after the other, which reduces the number of times to which the base plate may be exposed to a change of bag to the number of layers of adhesive, or by using a new bag with a fresh layer of adhesive, which renders the system more expensive in use.

One solution to this problem is disclosed in the applicants own WO 96/38106 in which is disclosed an ostomy collecting system which comprises a collecting bag having an inlet opening formed in a bag wall and with surrounding connecting elements for connection with a stoma in a user, and a carrier device for the collecting bag. The carrier device comprises a base plate for fastening on the user and a substantially annular first flange connected to the base plate via a first connecting section. The connecting elements comprise a substantially annular second flange, which is fixedly connected to the collecting bag via a substantially annular second connecting section and is designed for removable and adhesive connection with said first flange. The first and the second flanges are connected with the base plate and the collecting bag, respectively, in such a manner that the outer radius of said second connecting section exceeds the outer radius of said first connecting section by a value which at least equals the total thickness of the first and the second flanges. The adhesive connection between the collecting bag and the carrier device is provided by a layer of adhesive applied on said second flange and capable of repeated adhesion with the first flange, and the first and the second flanges are made from a flexible and resilient material.

Although this design provides a connection between carrier device and collecting bag, which is stable against displacement forces, and which acts as a shock absorbing element there is still a need for a even more safe solution in which the connecting surface between the collecting bag and the body side member is maintained largely independently of the deformation of the body side member caused by, for example, the user's movements, but which is nevertheless stable and continues to exhibit an even and flexible adhesive surface without wrinkles or gaps opening for passage of liquid between the flanges of the bag and the body side member. It is a further object that it should be possible to remove and reapply one or more bags repeatedly without any reduction in the life of the base plate and to reduce the necessary cleaning of the body side member when substituting the collecting bag.

SUMMARY OF THE INVENTION

The invention relates to a substantially annular flange for an ostomy collecting bag. The flange is divided in a radial direction into an inner portion and an outer portion by at least one opening therethrough in a substantially circular zone.

Furthermore, the invention relates to an ostomy collecting bag having a substantially annular flange connected thereto by a substantially annular connecting section. The annular flange is designed for removable and adhesive connection with a second flange connected with a body side member of an ostomy appliance by a second connecting section. The annular flange has at least one opening therethrough so as to divide the annular flange into an inner portion and an outer portion in a radial direction.

Still further, the invention relates to an ostomy appliance having a body side member with an adhesive wafer for securing the appliance to a user's skin, the wafer having a hole for receiving a stoma, and a separately exchangeable collecting bag. A substantially annular first flange is connected to the body side member via a first connecting section, and a substantially annular second flange is connected to the collecting bag via a second connecting section for adhesive connection with the first flange. The second flange has at least one opening therethrough that divides the second flange into an inner portion and an outer portion in a radial direction.

BRIEF DESCRIPTION OF THE DRAWINGS

The invention is disclosed more in detail with reference to the drawings in which.

DETAILED DESCRIPTION OF THE INVENTION

Figures 1, 2:
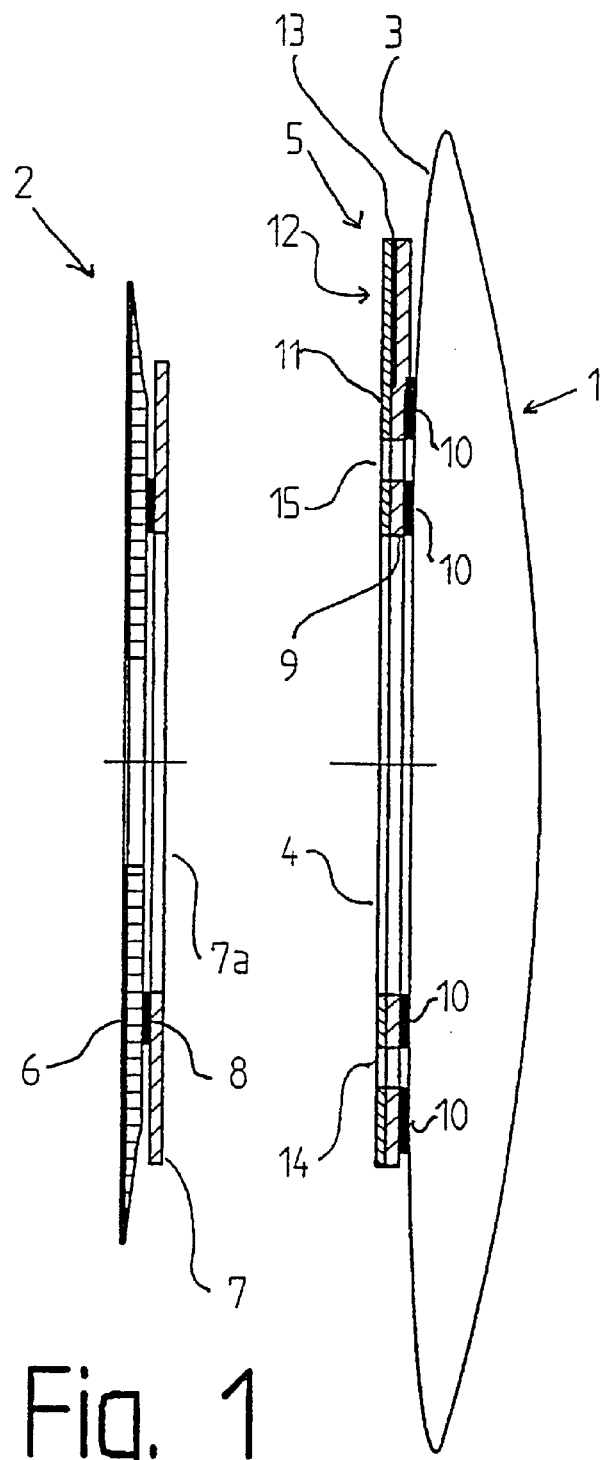
FIG. 1 shows a an embodiment of a body side member for use according to the invention for an ostomy collecting bag.
FIG. 2 shows section of a collecting bag 1 according to the invention along a line A—A as shown in FIG. 3.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention relates to an ostomy appliance comprising a body side member comprising an adhesive wafer or pad for securing the appliance to the user's skin, said wafer or pad having a hole for receiving a stoma, and a separately exchangeable receiving bag secured to the body side ostomy member for receiving secretions from the ostomy, wherein the body side member comprises a first substantially annular first flange connected to body side member via a first connecting section and the receiving bag comprises a second substantially annular second flange which is connected to the collecting bag via a substantially annular second connecting section and is designed for removable and adhesive connection with said first flange wherein the first and the second flanges are connected with the body side member and the collecting bag, respectively, and the adhesive connection between the collecting bag and the carrier device is provided by a layer of adhesive applied on said second flange and capable of repeated adhesion with the first flange, and the first and the second flanges are made from a flexible and resilient material, said ostomy appliance being characterised in that the second flange has one or more perforations in an essentially circular zone dividing the flange into an inner and an outer portion.

Due to erosion of the adhesive at the inner periphery of the hole in the flanges of the bag and the body side member there is an increased risk of formation of wrinkles or gaps from said periphery as there is a direct connection to the skin via the first connecting section transmitting the movements of the skin. If a wrinkle or gap is formed, it will proceed and eventually reach the outer periphery and form a canal giving a leak causing liberation of smell and pollution of the ostomates clothes.

It has been found that a circular zone of perforations will ensure that if a wrinkle or gap is formed at the inner periphery, it will not proceed to the outer periphery but stop in the zone of perforations where the flange is able to absorb the lateral movement without transmitting the same across the zone.

Furthermore, the body side member is preferably provided with a release liner onto which the adhesive may adhere releasably. When substituting the collecting bag, the surface is to be cleaned and using the present invention it is possible to let the second flange cover a larger part of the first flange protecting the same against contamination from the visceral contents minimising the necessary cleaning. It is noted that that the inner diameter of the foam flange has to be as little as possible, most preferable: very near the diameter of the stoma in order to minimise the skin irritation.

It is preferred that the outer radius of said second connecting section exceeds the outer radius of said first connecting section by a value which at least equals the total thickness of the first and the second flanges as such area outside the outer radius of said first connecting section will not bend or fold sharply in this area, because the release film is not in direct contact with the base plate on the skin.

In a preferred embodiment of the invention, the perforations are placed in an essentially circular zone corresponding to or larger than the outer radius of said first connecting section isolating the inner portion of the flange wherein wrinkles often occurs from the outer portion not being in direct contact with the base plate on the skin and thus improving the safety against leaks.

It is preferred that the perforations are in the form of two essentially circular openings occupying more than 50% of the circular zone, more preferred more than 60% and even more preferred more than 80%.

In embodiments of the invention wherein the circular openings leave one or more larger areas without interruption, it is preferred further one or more essentially circular holes are placed in the remaining part of the circular zone.

In a preferred embodiment of the invention the perforations are in the form a series of perforations placed in the circular zone. The perforations are preferably equidistant and leaving only narrow connections between the inner and outer portions of the flange. The perforations may e.g. be in the form of rectangular openings or preferably corresponding openings having rounded edges minimising the building-up of stress. In an especially preferred embodiment of the invention the perforations are in the form a series of triangular or trapezoid perforations placed with alternating orientation in the circular zone leaving only narrow connections between the inner and outer portions of the flange having a direction deviating from the radial direction in order to minimise the transmittance of stress across the circular zone. The edges of triangular or trapezoid perforations are preferably rounded. In an alternative embodiment the openings are in the form of two or more rows of essentially circular openings placed in two essentially circular zones having different diameters and wherein the individual perforations are not aligned with respect to the radial direction in a manner leaving only narrow connections between the inner and outer portions of the flange having a direction deviating from the radial direction.

The first and the second flanges are preferably formed as discs of a cellular plastic material, which provides a good shock absorbing and resilient action and also has the effect that the weight of the collecting system can be kept down.

In a second aspect, the invention relates to an ostomy collecting bag comprising a substantially annular flange which is connected to the collecting bag via a substantially annular connecting section and is designed for removable and adhesive connection with a flange connected with a body side member, characterised in that the flange has one or more perforations in an essentially circular zone dividing the flange into an inner and an outer portion.

An ostomy bag according to the invention will provide the advantages of the invention as explained above in combination with any body side member adapted to be connected to a collecting bag via an adhesive connection between the annular flange of the bag and a corresponding annular flange on the body side member.

It is preferred that the perforations are in the form of two essentially circular openings occupying more than 50% of the circular zone, more preferred more than 60% and even more preferred more than 80%.

In a preferred embodiment of the invention the perforations are in the form a series of perforations placed in the circular zone as explained above.

In a third aspect the invention relates to a flange for an ostomy collecting bag, characterised in that the flange has one or more perforations in an essentially circular zone dividing the flange into an inner and an outer portion. Such a flange may be used in a manner known per se for producing ostomy appliances and ostomy collecting bags having a connection between carrier device and collecting bag, which is stable against displacement forces.

DETAILED DESCRIPTION OF THE DRAWINGS

Reference is made to FIGS. 1 and 2 of the drawings showing an embodiment of an ostomy appliance according to the invention. The embodiment comprises a collecting bag 1 for collection of faeces and a body side member 2 for fastening the bag 1 around a stoma in the user's abdominal wall, and for this purpose has an inlet opening 4 in a bag wall 3. The bag 1 may either be closed as shown or be openable at the bottom for intermittent emptying of its contents. The inlet opening 4 is surrounded by connecting elements generally designated 5 for connecting the bag 1 with the body side member 2. The body side member comprises a base plate 6 which is designed to be adhered to the user's skin by means of a skin-friendly adhesive applied on the back of the base plate. The base plate 6 carries a first flange or base plate flange 7, in which is formed a hole 7a.

The base plate flange 7 is secured to the base plate 6 with a layer 8 of adhesive applied in a substantially annular connecting section having an internal diameter corresponding to that of the hole 7a in the base plate flange 7 and having an external diameter so that a rim portion of the flange 7 protrudes beyond the layer 8 of an adhesive. Of course, the flange 7 may also be fastened to the base plate 6 through other means, for example by welding. The base plate flange 7 may, for example, be moulded in a water-repellent cellular plastics material, such as ethylene vinyl acetate (EVA) or polyurethane (PUR), with closed cells so that the cellular plastic material does not absorb liquid.

The fastening elements 5 on the bag 1 are constructed from a second flange or bag flange 9 having one or more perforations 14, 15 and which, in the embodiment shown, is secured to the bag wall 3 by means of a substantially annular connecting section in the form of a layer 10 of an adhesive in such a manner that a rim portion of the bag flange 9 protrudes beyond the layer 10 of adhesive. The outer radius of the layer 10 of adhesive exceeds the outer radius of the layer 8 of adhesive between the base plate flange 7 and the base plate 6 by a value at least equalling the total thickness of the base plate flange 7 and the bag flange 9. Of course, the bag flange 9 may also be fastened to the bag wall 3 through other means, for example by welding, and like the base plate flange 7 it consists of a moulded cellular plastic material, such as EVA cellular plastic or PUR cellular plastics. On the side facing away from the bag, the flange 9 is coated over substantially all its surface with a thin, washable layer of adhesive (not shown), which may, for example, be a hydrogel adhesive, an acrylate adhesive or an adhesive of the hot-melt type. The layer of adhesive is applied in a thin layer, partly to keep thickness low, and partly to maintain the flexibility and resilience of the bag flange. This application may be effected, for example, by coating, spraying or application in a suitable pattern. In the delivery state of the bag, the layer of adhesive is covered by a release liner 11. The section of flange 9 of the bag 1 shown in FIG. 2 is taken along the line A—A of a flange as shown in FIG. 3.

The bag flange 9 preferably has a protruding part or ear 12 facilitating the removal of the bag by providing a handle or grip for handling the bag. In such an area, the adhesive is preferably covered by a cover layer 13.

When the collecting system according to the invention is used, the body side member 2 is arranged on the user's abdomen, the base plate 6 being, placed against the user's skin, and the stoma being passed out through the hole 4. The release liner 11 of the collecting bag is removed from the layer of adhesive, which is subsequently adhered to the base plate flange 7 of the body side member around the stoma.

Figure 3:
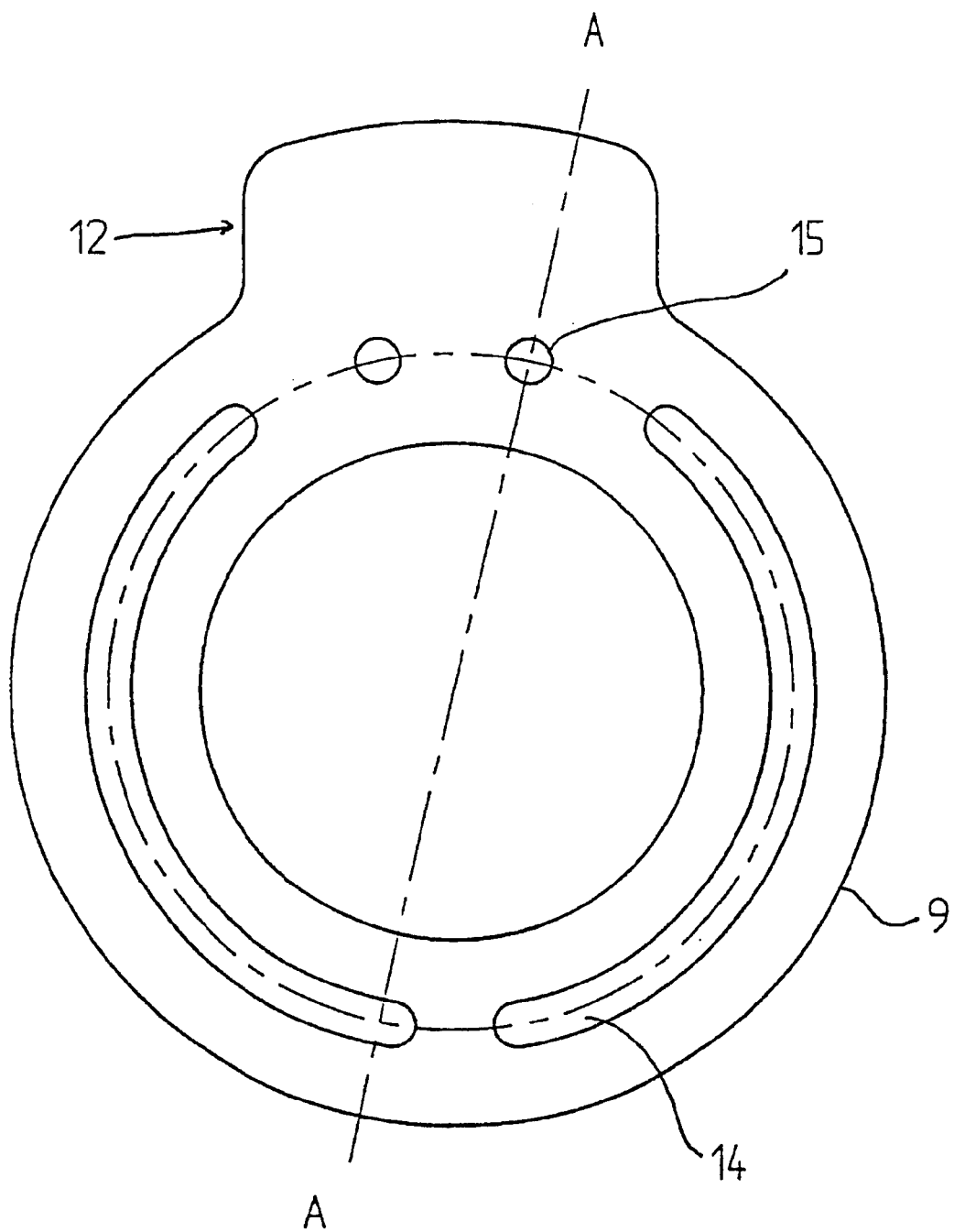
FIG. 3 shows an embodiment of a flange for use according to the invention for an ostomy bag.

FIG. 3 shows an embodiment of a flange 9 according to the invention having a protruding part or ear 12 and having perforations 14, 15 in a circular zone having a diameter larger than the diameter of the connection zone 8 of the body side member of FIG. 1. In this embodiment, perforations of different shapes are present, namely elongated perforations or openings 14 and circular openings 15. The line A—A indicates the line of section of the flange shown in FIG. 1.

Figure 4:
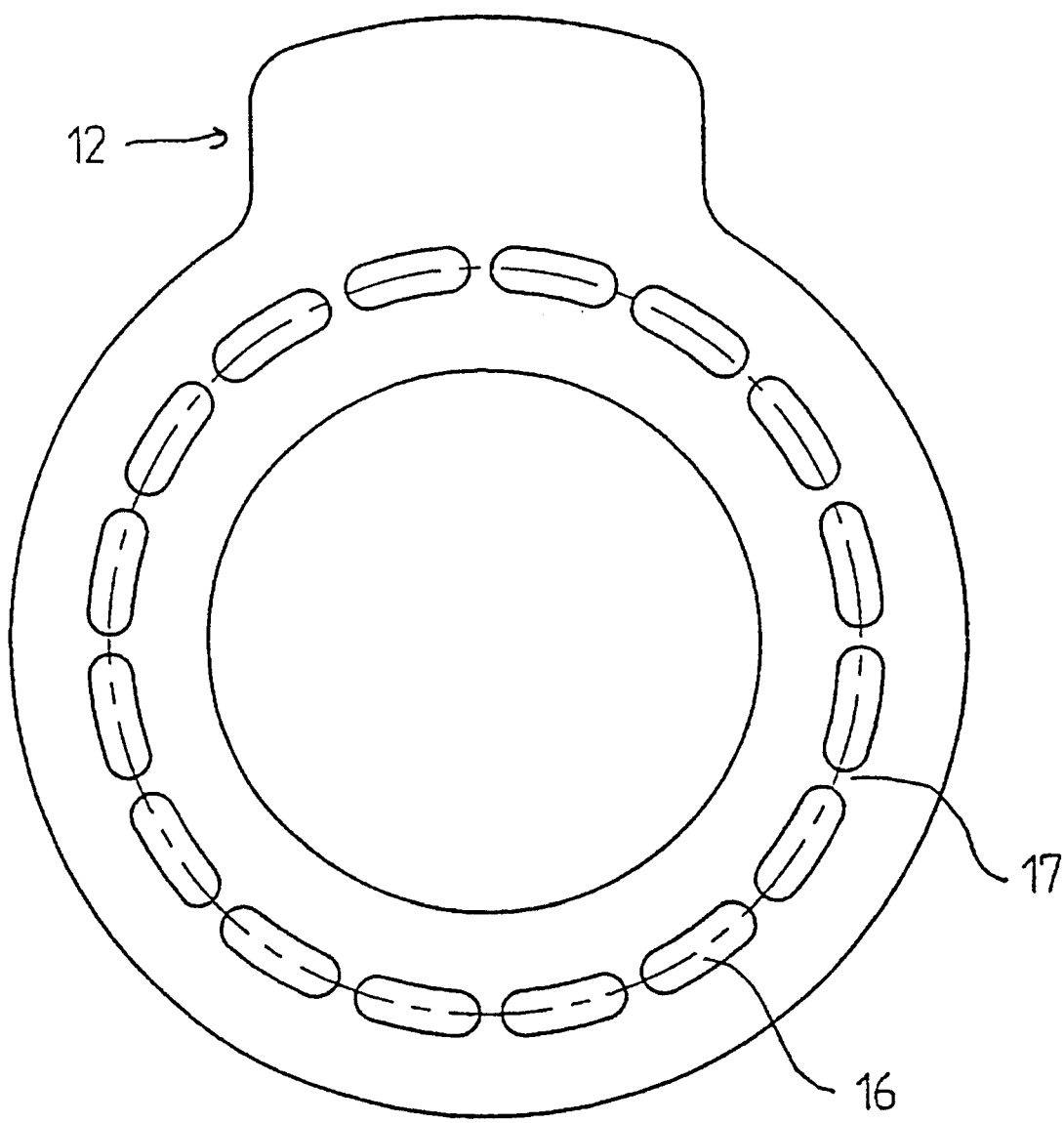
FIG. 4 shows another embodiment of a flange for use according to the invention for an ostomy collecting bag.

FIG. 4 shows another embodiment of a flange according to the invention having a protruding part or ear 12 and having a series of essentially similar perforations 16 placed in a circular zone. The perforations are placed equidistantly leaving only narrow connections 17 between the inner and outer portions of the flange.

Figure 5:
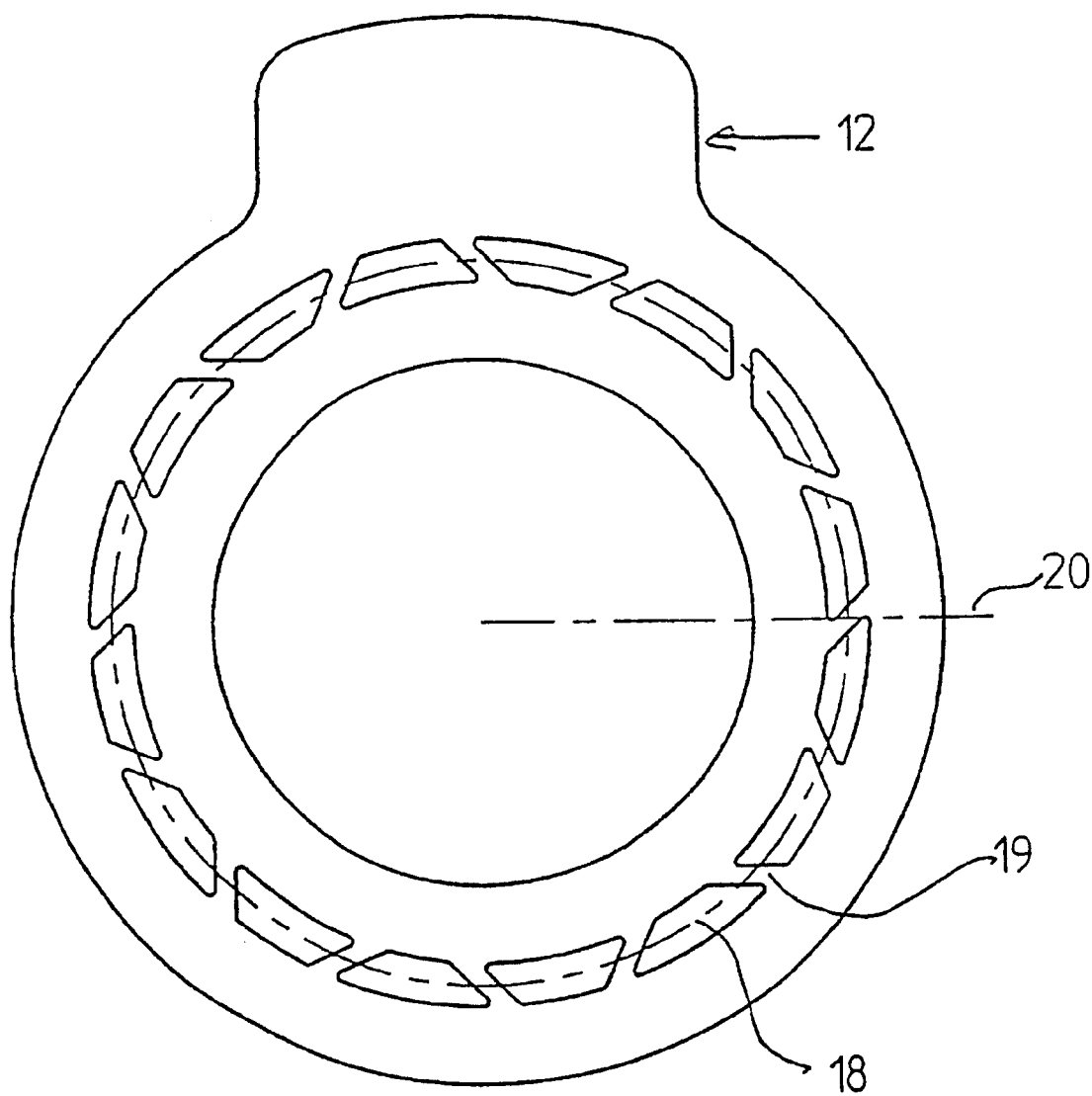
FIG. 5 shows yet another embodiment of a flange for use according to the invention for an ostomy collecting bag.

FIG. 5 shows a further embodiment of a flange according to the present invention having a protruding part or ear 12 and having a series of essentially similar trapezoidal-shaped perforations 18 placed in a circular zone. The perforations are placed equidistantly and alternating leaving only narrow connections 19 between the inner and outer portions of the flange having a direction deviating from the radial direction in order to minimise the transmittance of stress across the circular zone as indicated by the radius 20.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A substantially annular flange for an ostomy collecting bag, said flange being divided in a radial direction into an inner portion and an outer portion by at least one opening therethrough.

2. The flange as set forth in claim 1, wherein said flange is connected to said collecting bag by a substantially annular connecting section positioned on said inner portion and said outer portion and adjacent each side of said opening.

3. The flange as set forth in claim 1, wherein said opening includes a plurality of openings spaced along a circular zone of said flange.

4. The flange as set forth in claim 1, wherein said opening is substantially annular and occupies more than 50% of a circular zone of said flange.

5. The flange as set forth in claim 4, further comprising at least one substantially circular opening placed in a remaining part of said circular zone.

6. An ostomy collecting bag and flange comprising a substantially annular flange connected to the collecting bag by a substantially annular connecting section and designed for removable and adhesive connection with a second flange connected with a body side member by a second connecting section, said annular flange having an opening therethrough in a circular zone thereof so as to radially divide said annular flange into an inner portion and an outer portion.

7. The ostomy collecting bag as set forth in claim 6, wherein said opening is substantially annular and occupies more than 50% of said circular zone.

8. The ostomy collecting bag as set forth in claim 6, wherein said circular zone is at least as large as an outer radius of said second connecting section.

9. The ostomy collecting bag as set forth in claim 6, wherein said opening includes a plurality of openings spaced from one another along said circular zone.

10. The ostomy collecting bag as set forth in claim 9, wherein said plurality of openings include an elongated opening and a circular opening spaced from one another.

11. The ostomy collecting bag as set forth in claim 9, wherein said plurality of openings include a series of similar openings spaced substantially equidistantly leaving narrow connections between said inner portion and said outer portion.

12. An ostomy appliance comprising:
a body side member having an adhesive wafer for securing the appliance to a user's skin, said wafer having a hole for receiving a stoma, a first flange connected to said body side member via a first connecting section;
a separately exchangeable collecting bag removably secured to the body side member for receiving secretions from the stoma by a substantially annular second flange connected to said collecting bag via a second connecting section for adhesive connection with said first flange, said second flange having at least one opening therethrough radially dividing said second flange into an inner portion and an outer portion.

13. The ostomy appliance as set forth in claim 12, wherein an outer radius of said second connecting section is greater than an outer radius of said first connecting section by a value not less than a total thickness of said first and second flanges.

14. The ostomy appliance as set forth in claim 12, wherein said opening includes a plurality of openings annularly spaced from one another.

15. The ostomy appliance as set forth in claim 14, wherein said plurality of openings include an elongated opening and a circular opening.

16. The ostomy appliance as set forth in claim 14, wherein said plurality of openings include a series of similar openings spaced substantially equidistantly leaving only narrow connections between said inner portion and said outer portion.

17. An ostomy collecting bag and flange comprising a substantially annular flange connected to the collecting bag by a substantially annular connecting section and designed for removable and adhesive connection with a body side member, said annular flange having at least one opening positioned radially about midway between inner and outer edges of said flange to reduce wrinkling of said flange and resulting passage of fluids.

18. The ostomy collecting bag and flange as set forth in claim 17, wherein said at least one opening is elongated and generally tracks the annular shape of said annular flange.

19. The ostomy collecting bag and flange as set forth in claim 17, wherein said flange includes a plurality of openings annularly spaced from one another.

20. The ostomy collecting bag and flange as set forth in claim 19, wherein said plurality of openings includes a series of trapezoidal-shaped openings spaced substantially equidistantly, leaving narrow connections between inner and outer portions of said flange that deviate from a radial direction.

* * * * *